US011009383B2

(12) United States Patent
Cumbie et al.

(10) Patent No.: US 11,009,383 B2
(45) Date of Patent: May 18, 2021

(54) FLUID PROPERTY SENSING WITH ELECTRODES (71) Applicant: HEWLETT-PACKARD DEVELOPMENT COMPANY, L.P., Houston, TX (US)

(72) Inventors: Michael W. Cumbie, Corvallis, OR (US); Chien-Hua Chen, Corvallis, OR (US); Greg Scott Long, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 159 days.

(21) Appl. No.: 16/092,572

(22) PCT Filed: Apr. 21, 2016

(86) PCT No.: PCT/US2016/028633
§ 371 (c)(1),
(2) Date: Oct. 10, 2018

(87) PCT Pub. No.: WO2017/184144
PCT Pub. Date: Oct. 26, 2017

(65) Prior Publication Data
US 2019/0120678 A1 Apr. 25, 2019

(51) Int. Cl.
*G01F 23/26* (2006.01)
*B41J 2/195* (2006.01)
(Continued)

(52) U.S. Cl.
CPC .......... *G01F 23/263* (2013.01); *B41J 2/1753* (2013.01); *B41J 2/17513* (2013.01);
(Continued)

(58) Field of Classification Search
CPC .... G01N 27/221; G01N 27/226; G01N 33/32; G01F 23/263; G01F 23/265;
(Continued)

(56) References Cited

U.S. PATENT DOCUMENTS 4,626,874 A 12/1986 Murai et al.
5,194,133 A * 3/1993 Clark ...................... G01N 30/64
204/403.01

(Continued)

FOREIGN PATENT DOCUMENTS

CN 1488509 A 4/2004
CN 2645049 9/2004
(Continued)

OTHER PUBLICATIONS

Chen, C. T.; "A New Method of Ink Level Detection for Inkjet Printers by Pressure Conditions"; Proceedings for NIP & Digital Fabrication Conference; Jan. 1, 1999.

*Primary Examiner* — Paul M. West
(74) *Attorney, Agent, or Firm* — Fabian VanCott (57) ABSTRACT In one example in accordance with the present disclosure a fluid property sensing device is described. The fluid property sensing device includes a substrate having a trench formed therein. The trench includes a bottom surface and opposite side surfaces. A first electrode is disposed on a first side surface of the trench and a second electrode is disposed on a second side surface of the trench. The first electrode and second electrode form a capacitor to measure a complex impedance of a fluid that fills a space between the first electrode and the second electrode. This complex impedance indicates a property of the fluid. A fluid level sensing die, having a number of fluid level sensing components disposed thereon, may be attached to the substrate, preferably in such a way that the fluid level sensing die is surrounded by the trench. In this way the surface area of the electrodes pro- (Continued)

vided in the trench can be increased. The number of level sensing components may be thermal sensing components.

20 Claims, 8 Drawing Sheets

(51) Int. Cl.
    *B41J 2/175*     (2006.01)
    *G01N 27/22*     (2006.01)
    *G01N 33/32*     (2006.01)
    *G01F 23/24*     (2006.01)

(52) U.S. Cl.
    CPC ............ *B41J 2/17566* (2013.01); *B41J 2/195* (2013.01); *G01F 23/265* (2013.01); *G01F 23/268* (2013.01); *G01N 27/221* (2013.01); *G01N 27/226* (2013.01); *G01N 33/32* (2013.01); *B41J 2002/17579* (2013.01); *G01F 23/247* (2013.01); *G01F 23/261* (2013.01)

(58) Field of Classification Search
    CPC ..... G01F 23/268; B41J 2/17566; B41J 2/195; B41J 2002/17579
    See application file for complete search history.

(56) References Cited

U.S. PATENT DOCUMENTS

| | | |
|---|---|---|
| 5,682,184 A | 10/1997 | Stephany |
| 6,929,343 B2 | 8/2005 | Farr |
| 7,556,326 B2 | 7/2009 | Knierim |
| 7,896,454 B2 | 3/2011 | Eguchi |
| 8,065,913 B2 | 11/2011 | McCracken |
| 8,091,993 B2 | 1/2012 | Gilson et al. |
| 2004/0223021 A1 | 11/2004 | Farr et al. |
| 2005/0120791 A1 | 6/2005 | Carlson |
| 2005/0126282 A1 | 6/2005 | Maatuk |
| 2005/0243110 A1 | 11/2005 | Takahashi |
| 2007/0110612 A1* | 5/2007 | Ito .................. A61M 1/3638 422/44 |
| 2012/0306974 A1 | 12/2012 | Nicholson, III |
| 2013/0068015 A1 | 3/2013 | Sinha |
| 2015/0013646 A1 | 1/2015 | Qi |

FOREIGN PATENT DOCUMENTS

| | | |
|---|---|---|
| CN | 2769861 | 4/2006 |
| CN | 101213443 | 7/2008 |
| CN | 101561307 | 10/2009 |
| CN | 201892559 | 7/2011 |
| CN | 103196517 | 7/2013 |
| CN | 105025809 | 11/2015 |
| CN | 105486735 | 4/2016 |
| WO | WO9640524 | 12/1996 |

\* cited by examiner

FLUID PROPERTY SENSING WITH ELECTRODES

BACKGROUND

Fluid reservoirs are used to contain all sorts of fluids. For example in printing systems, print cartridges hold stores of printing fluid such as ink. The ink, or other printing fluid from a reservoir, is supplied to a printhead which deposits the printing fluid onto a print medium, such as paper. The different fluids contained within a fluid reservoir have different properties, which are indicative of the type of fluid contained therein.

BRIEF DESCRIPTION OF THE DRAWINGS

The accompanying drawings illustrate various examples of the principles described herein and are a part of the specification. The illustrated examples are given merely for illustration, and do not limit the scope of the claims.

Throughout the drawings, identical reference numbers designate similar, but not necessarily identical, elements.

DETAILED DESCRIPTION

Fluid reservoirs are used to hold various types of fluids. For example, in a printing system, an ink cartridge stores a volume of ink. This ink is passed to a printhead for deposition onto a print medium to form text or images on the print medium.

As printing fluid is deposited onto a print medium, the fluid reservoir is depleted of printing fluid. Accordingly, the print fluid within a fluid reservoir may be refilled, or the fluid reservoir replaced with a new, full reservoir. While the use of fluid reservoirs, specifically printing fluid reservoirs that can be replaced or refilled, have enhanced printing capabilities for business and residential use, some characteristics impact a more complete implementation. For example, there are a wide variety of printing fluids with just as wide a variety of quality among the printing fluids. Some printing fluids that are refilled into a reservoir, or that are contained within a replaceable reservoir, may be of a lesser quality than an original manufacturer's printing fluid. Such reduced printing fluid quality logically affects print quality. These lower quality printing fluid products may lead to customer dissatisfaction due to a reduction of the quality of printing. If such printing fluid is counterfeit, this customer dissatisfaction may be mistakenly directed to another entity. Thus it is in the interest of manufacturers to be able to control their product and prevent the introduction of counterfeit, or otherwise undesirable printing fluids from being used in their products.

Accordingly, the present specification describes a fluid property sensing device. As mentioned above, each fluid has a distinct signature. One component of such a signature is the dielectric constant, which impacts the fluids ability to conduct electricity. In the fluid property sensing system a pair of spaced electrodes form a capacitor. As the pair of electrodes are immersed in a particular fluid such as ink, a complex impedance measurement of the fluid can be taken, which complex impedance can be used to identify the particular fluid. For example, using a lookup table, the measured values can be compared to a database of known values to identify a particular fluid. This property, which is akin to a fingerprint, can be used to distinguish between counterfeit and genuine fluids as well as high and low quality fluids.

Specifically, the present specification describes a fluid property sensing device. The device includes a substrate having a trench formed therein. The trench has a bottom surface and opposite side surfaces. A first electrode is disposed on a first side surface of the trench and a second electrode is disposed on a second side surface of the trench. The first electrode and second electrode form a capacitor to detect a complex impedance of a fluid that fills a space between the first electrode and the second electrode. The complex impedance identifies the fluid by indicating a property of the fluid.

The present specification also describes a method for forming a fluid property sensing device. A trench is formed in a substrate. A first side surface of the trench is plated to form a first electrode and a second side surface of the trench is plated to form a second electrode. The first electrode and the second electrode form a capacitor defined by the side surfaces and gap between the side surfaces. The electrodes are then electrically coupled to electrical interconnects.

The present specification describes a fluid property sensing device. The fluid property sensing device includes a substrate having a trench formed therein. The substrate provides electrical connectivity between a sensing die, a capacitor, and electrical interconnects and also provides mechanical protection of a fluid level sensing die. The fluid property sensing device also includes the fluid level sensing die that is disposed on the substrate. A number of sensing components are disposed on the fluid level sensing die. The number of sensing components detect a fluid level in a fluid reservoir. A capacitor of the fluid property sensing device is defined by electrodes placed on walls of the trench. The electrodes are used to detect a property of the fluid in the fluid reservoir. An integrated circuit of the fluid property sensing device outputs data collected form the number of sensing components to the electrical interconnects and the electrical interconnects output data collected from the integrated circuit and the capacitor. A sealing device seals the fluid property sensing device against a fluid reservoir in which the fluid property sensing device is inserted.

In one example, using such a device for sensing a fluid property 1) provides additional data, and therefore control over, fluids used in a fluid reservoir; 2) provides fluid property sensing via a device produced by a low cost, high volume, and simple manufacturing process; 3) provides a sensing device that supports fluid level sensing and fluid property sensing; 4) provides a large electrode to provide increased signal sensitivity; 5) provides a high resolution and high performance fluid level and property sensing platform; 6) supports multiple processes for detecting fluid levels; and 7) provides a fluid property sensing device that can be integrated as a module or on an interior surface of a reservoir; and 8) results in increased customer satisfaction due to the increased performance. However, it is contemplated that the devices disclosed herein address other matters and deficiencies in a number of technical areas.

As used in the present specification and in the appended claims, the term "property" refers to characteristics of a fluid, Examples of properties include a fluid type, a fluid color, a fluid viscosity, and the colorant used in a fluid, among other properties.

Still further, as used in the present specification and in the appended claims the term "complex impedance" refers to a frequency domain ratio of a voltage and a current. In other words, it is a voltage-current ratio at a particular frequency, which has both amplitude and phase information of the voltage and current. The complex impedance of a fluid refers to an imaginary or complex number component of a total impedance. The total impedance of a fluid has two parts, a real component and an imaginary component. The different components contain different information about the dielectric/molecular behavior of the fluid being measured.

As used in the present specification and in the appended claims, the term "a number of" or similar language is meant to be understood broadly as any positive number including 1 to infinity.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an example" or similar language indicates that a particular feature, structure, or characteristic described in connection with that example is included as described, but may not be included in other examples.

Figure 1:
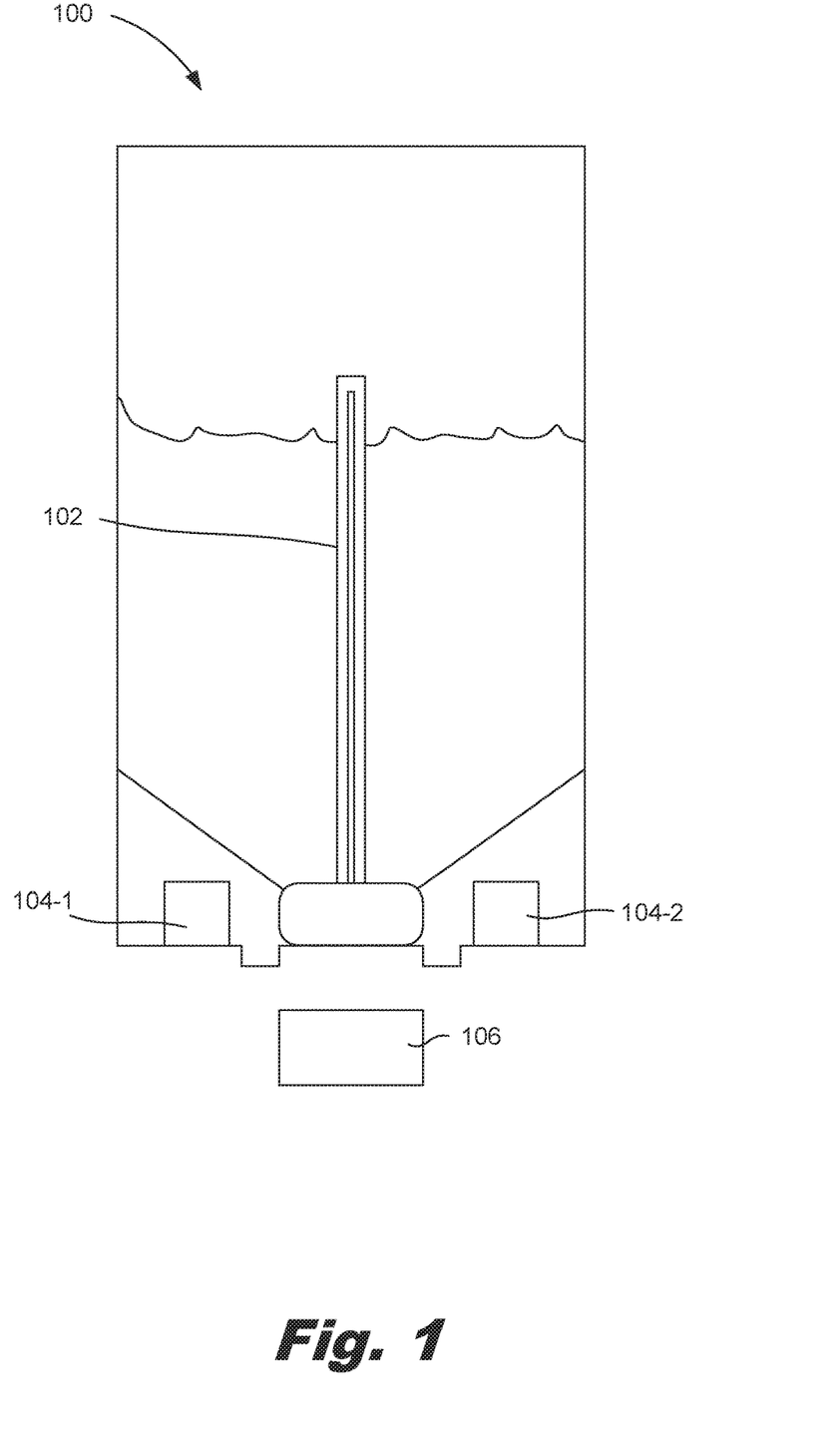
FIG. 1 is a cross-sectional view of a fluid property sensing device as inserted into a fluid reservoir, according to one example of the principles described herein.

Turning now to the figures, FIG. 1 is a cross-sectional view of a fluid property sensing device (102) as inserted into a fluid reservoir (100), according to one example of the principles described herein. A fluid reservoir (100) may be any container that holds a fluid. For example, a printing system implements a print cartridge, wherein the fluid stored therein is ink. The fluid reservoir (100) retains fluid and supplies it to a system for further operation. For example, in a printing system, via a number of fluid interconnects (104-1, 104-2), the fluid within the fluid reservoir (102) is supplied to a printhead to be deposited on a print medium. As fluid is used, it is depleted from the fluid reservoir (100). Such fluid may be refilled, or the entire fluid reservoir (100) replaced. To ensure control over the print fluid in general, for example to ensure that genuine print fluids or reservoirs (100) are being used, and not counterfeit fluids or reservoirs (100), a fluid property sensing device (102) is used. With such a fluid property sensing device (102), greater control over the printing fluid and printing process in general is provided. For example, a manufacturer, having information about different print fluid properties, can manage the use of, or prevent the use of, various printing fluids by first identifying the fluid, and then controlling the printing system based on the identification of the fluid.

As depicted in FIG. 1, the fluid property sensing device (102) is disposed within the fluid reservoir (100). While FIG. 1 depicts the fluid property sensing device (102) as part of a module that is inserted into the middle of the fluid reservoir, the fluid property sensing device (102) may also be disposed on an interior wall of the fluid reservoir (100) as described below. The fluid property sensing device (102) has electrical interconnects to output data collected from the number of sensing components. These electrical interconnects of the fluid property sensing device (102) mate with, and electrically couple with a corresponding electrical interconnect (106) on a separate component such that data collected from the fluid property sensing device (102) can be passed to a corresponding system and analyzed and used to control operation of the associated system. For example, the fluid property sensing device (102) as described herein can be used in the detection of counterfeit fluid as well as ensuring that the proper fluid reservoir (FIG. 1, 102) is installed in an associated printing device.

Figure 2A:
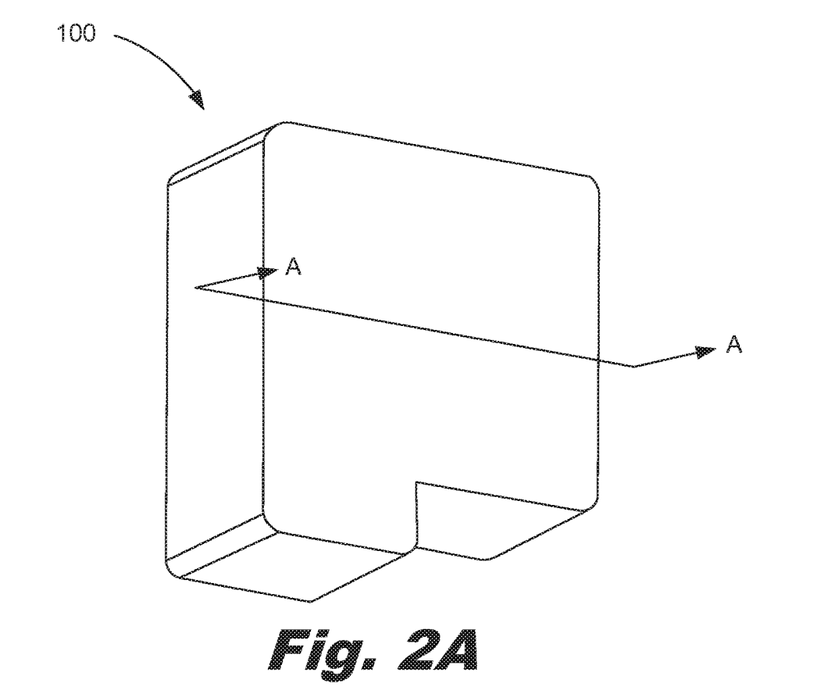
FIGS. 2A and 2B are isometrics view of a fluid property sensing device as disposed on a wall of a fluid reservoir, according to one example of the principles described herein.
Figure 2B:
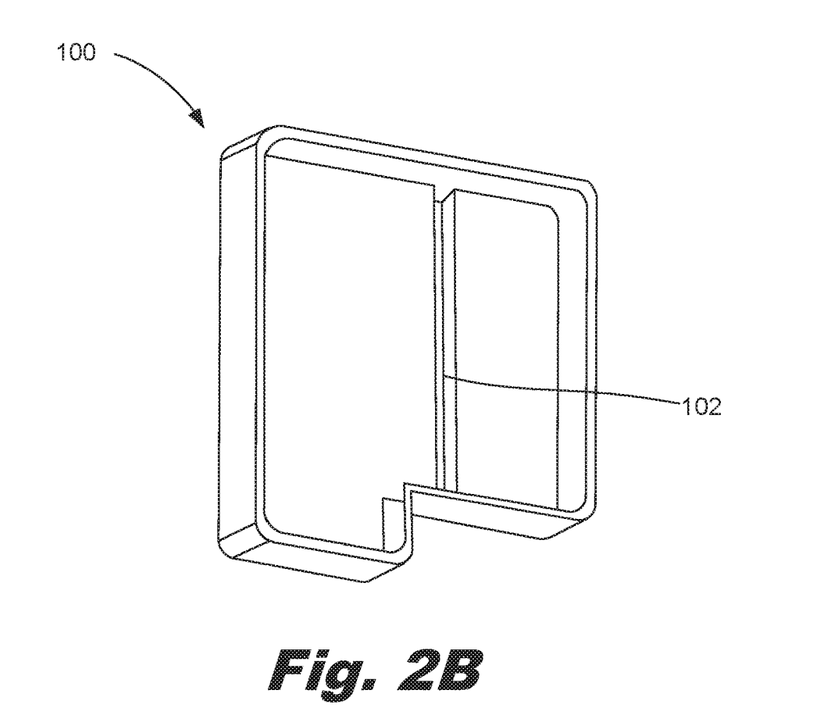

FIGS. 2A and 2B are isometrics view of a fluid property sensing device (102) as disposed on a wall of a fluid reservoir (100). Specifically, FIG. 2A is an isometric outside view of the fluid reservoir (100) and FIG. 2B is an isometric cross sectional view of the fluid reservoir (100) taken along the line "A-A", In general, the fluid property sensing device (102) includes a substrate. In the example depicted in FIG. 2B, the substrate is an interior wall of the fluid reservoir (100). The substrate has a trench formed therein having a bottom surface and opposite side surfaces. Electrodes disposed on the side surfaces of the trench form the metal plates that define a capacitor separated by a gap, the gap being defined by the bottom surface of the trench. As fluid fills the gap between the electrodes, a complex impedance measurement is taken. This complex impedance is indicative of a property of the fluid, which property can be used to identify the type of fluid within the fluid reservoir (100). Examples of properties that can be detected are pigmentation, colorants used, and printing fluid family, among other properties. In other words, a detected property may be any characteristic of a fluid that distinguishes the fluid from another fluid. The property may be identified via the permittivity, or complex impedance of the fluid. Thus, using the complex impedance measurement, the fluid within the fluid reservoir (102) may be identified.

In such a fashion an entity, for example a manufacturer, can verify the type of fluid being used in the fluid reservoir (100). With such verification in hand, the manufacture can perform control operations to ensure that the fluid reservoir (100) functions when a predetermined type of fluid, i.e., produced by the manufacturer, approved for a certain type of printing, or having a certain quality, is present in the fluid reservoir (102). Moreover, the design of the fluid property sensing device (102), i.e., being a plated trench on the sidewall of a fluid reservoir (102), provides a simple construction that can reliably indicate the property of a fluid within a fluid reservoir (102).

Figure 3A:
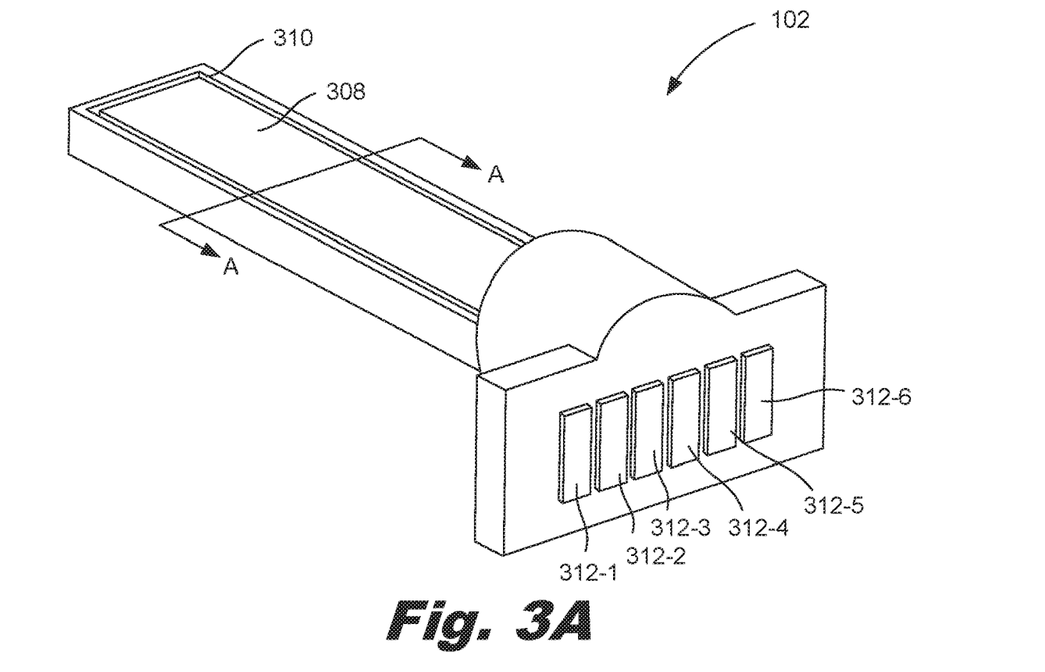
FIGS. 3A and 3B are views of the fluid property sensing device, according to one example of the principles described herein.
Figure 3B:
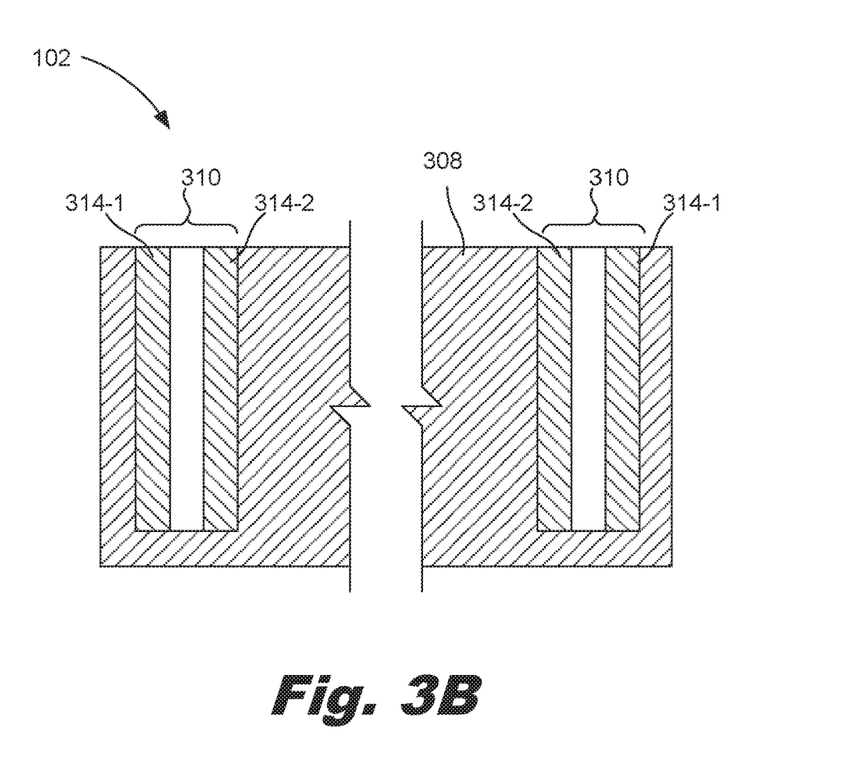

FIGS. 3A and 3B are views of the fluid property sensing device (102), according to one example of the principles described herein. Specifically, FIG. 3A is an isometric view of the fluid property sensing device (102) and FIG. 3B is a cross-sectional view of the fluid property sensing device (102) taken along the line "A-A" from FIG. 3A. As described above, the fluid property sensing device (102) includes a substrate (308). As described in FIGS. 2A and 2B, the substrate (308) may be an interior wall of the fluid reservoir (FIG. 1, 100). In the example depicted in FIGS. 3A and 3B, the substrate (308) is modular. That is the fluid property sensing device (102) is part of a module that is to be inserted into the fluid reservoir (FIG. 1, 100) as depicted in FIG. 1.

The substrate (308) may be comprise any number of materials including plastic, silicon, glass polymers, FR4, glass-reinforced epoxy laminate. The substrate (308) may also take any number of forms such as a sheet, tube, rod, printed circuit board, or other rigid member. In one example, the substrate (308) includes a composite material of woven fiberglass cloth with an epoxy resin binder. For example, the substrate (308) may be a printed circuit board having embedded electrical traces and contact pads to facilitate electrical connection between various components mounted on the substrate (308) such as the electrodes, sensing components, sensing dies, and integrated circuits. Disposed on the substrate (308) are electrical interconnects (312-1, 312-2, 312-3, 312-4, 312-5, 312-6) to output data collected from the electrodes and other sensing components. For example, the capacitor may output a complex impedance that is indicative of the property of fluid that fills the gap between the electrodes (314-1, 314-2), thus allowing identification of the fluid in the fluid reservoir (FIG. 1, 100). This information is then passed to the electrical interconnects (312) to be output to an external device that can use the outputted data. For example, the fluid property information gathered from the electrodes (314) can be used to prevent the printing when a counterfeit printing fluid is detected within the fluid reservoir (FIG. 1, 100).

Each side surface of the trench (310) is plated to form an electrode (314). Specifically a first electrode (314-1) is disposed on a first side surface of the trench (310) and a second electrode (314-2) is disposed on a second side surface of the trench (310). The electrodes (314) form the metal plates of a capacitor with the bottom surface defining the air gap between the metal plates. As described above, each fluid, ink for example, has its own unique signature in the Fourier domain and can be detected with complex impedance measurements. This complex impedance measurement varies between ink colors, families, colorant type, etc. Accordingly, by measuring this complex impedance of the fluid that fills the gap between the first electrode (314-1) and second electrode (314-2), and via comparison to a database of associations between complex impedance measurements and fluid properties, a property of the fluid can be determined based on the complex impedance measurement coming from the capacitor, and the fluid identified.

In some examples, these parallel electrodes (314-1, 314-2) could be formed at the same time as metal traces and the electrical interconnects (312). Examples of metals used as metal traces include gold and copper among other metals. Forming all these components at the same time simplifies manufacturing by reducing the number of distinct operations and by reducing the number of machines used to perform these manufacturing operations.

The dimensions of the electrodes (314) affect the accuracy of the fluid property sensing device (102). For example, the complex impedance signal strength is proportional to the size of the electrodes (314). Accordingly, the gap between the electrodes (314) may be greater than 300 micrometers wide. For example, the gap may be 500 micrometers wide. While specific widths are mentioned, other widths are also possible, which may be less than 300 micrometers. Such a width of the gap protects against shorting of the electrodes (314) that may result as pigments conglomerate between the electrodes (314). It should be noted, that the principles described in FIGS. 3A and 3B, specifically that of metal plating the side walls of the trench (310) can be applicable to the trench described in connection with FIG. 2. While specific reference has been made to 500 and 300 micrometer widths, different sizes of gaps may be used as well.

Figure 4:
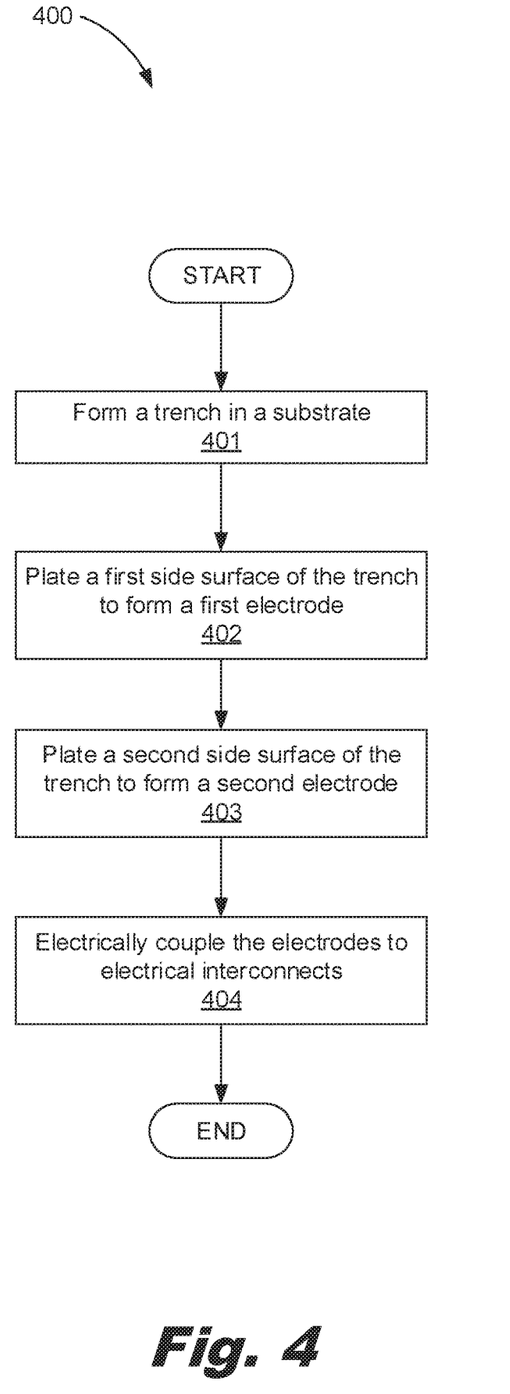
FIG. 4 is a flowchart illustrating a method of forming a fluid property sensing device, according to one example of the principles described herein.

FIG. 4 is a flowchart illustrating a method (400) of forming a fluid property sensing device (FIG. 1, 102), according to one example of the principles described herein. According to the method (400), a trench (FIG. 3, 310) is formed (block 401) in the substrate (FIG. 3, 308). The trench (FIG. 3, 310) has a bottom surface and side walls. The trench (FIG. 3, 310) can be formed in any number of methods. For example, the substrate (FIG. 3, 308) may be plastic, or other material, and the trench (FIG. 3, 310) may be formed in the substrate (FIG. 3, 308) via injection molding for example. In other examples, a flat substrate (FIG. 3, 308) is provided, and a router, laser, or other cutting device removes material from the substrate (FIG. 3, 308) to form the trench (FIG. 3, 310). While specific reference is made to a few techniques for forming the trench (FIG. 3, 310)) any number of methods may be used to form the trench (FIG. 3, 310).

The side surfaces of the trench (FIG. 3, 310) are then plated to form the electrodes (FIG. 3, 314). Specifically, a first side surface is plated (block 402) to form a first electrode (FIG. 3, 314-1) and a second side surface is plated (block 403) to form a second electrode (FIG. 3, 314-2). The electrodes (FIG. 3, 314) may be formed in any number of fashions. For example, a patterned metal seed layer can be deposited using any number of methods such as laser direct structuring which uses a laser to activate a plastic surface for metal seed layer deposition and plating on a three-dimensional surface. In another example, three-dimensional metal routing can be used which involves spraying/dip coating the surface, laser writing to the surface, and plating the surface. In another example, metal traces may be deposited using electrostatic dispensing which uses electrostatic force to break the surface tension of a nozzle tip to deposit metal surfaces. In another example, a shadow mask can be used in conjunction with an electron beam or metal sputtering deposition processes to form seed layers on the trench sidewall. In some examples, on top of this metal seed layer, a thicker copper trace can be plated and sealed with a gold or palladium protective layer. As described above, the second side surface and the first side surface may be plated (block 402, 403) at the same time as the formation of the electrical interconnects (FIG. 3, 312) and any mechanical traces that electrically couple the electrodes (FIG. 3, 314) to the electrical interconnects (FIG. 3, 312). Doing so may simplify manufacturing as less machines and fewer distinct operations are performed to complete these operations.

With the electrodes (FIG. 3, 314) formed, the electrodes (FIG. 3, 314) are electrically coupled (block 404) to the electrical interconnects (FIG. 3, 312). As described above, the electrical interconnects (FIG. 3, 312) pass information gathered from the electrodes (FIG. 3, 314) to another device such as a controller that can perform a number of functions based on the gathered information, such as preventing printing when an unauthorized, or otherwise prohibited fluid or fluid reservoir, is being inserted into a printing device. Such electrical coupling may involve wire-bonding the electrodes (FIG. 3, 314) to the electrical interconnects (FIG. 3, 312), or providing other electrical paths between the electrodes (FIG. 3, 314) of the capacitor and the electrical interconnects (FIG. 3, 312). The method (400) as described herein is simple, cost effective, and allows for flexibility in design such that large surface area electrodes can be used which provides enhanced fluid property sensing.

Figure 5:
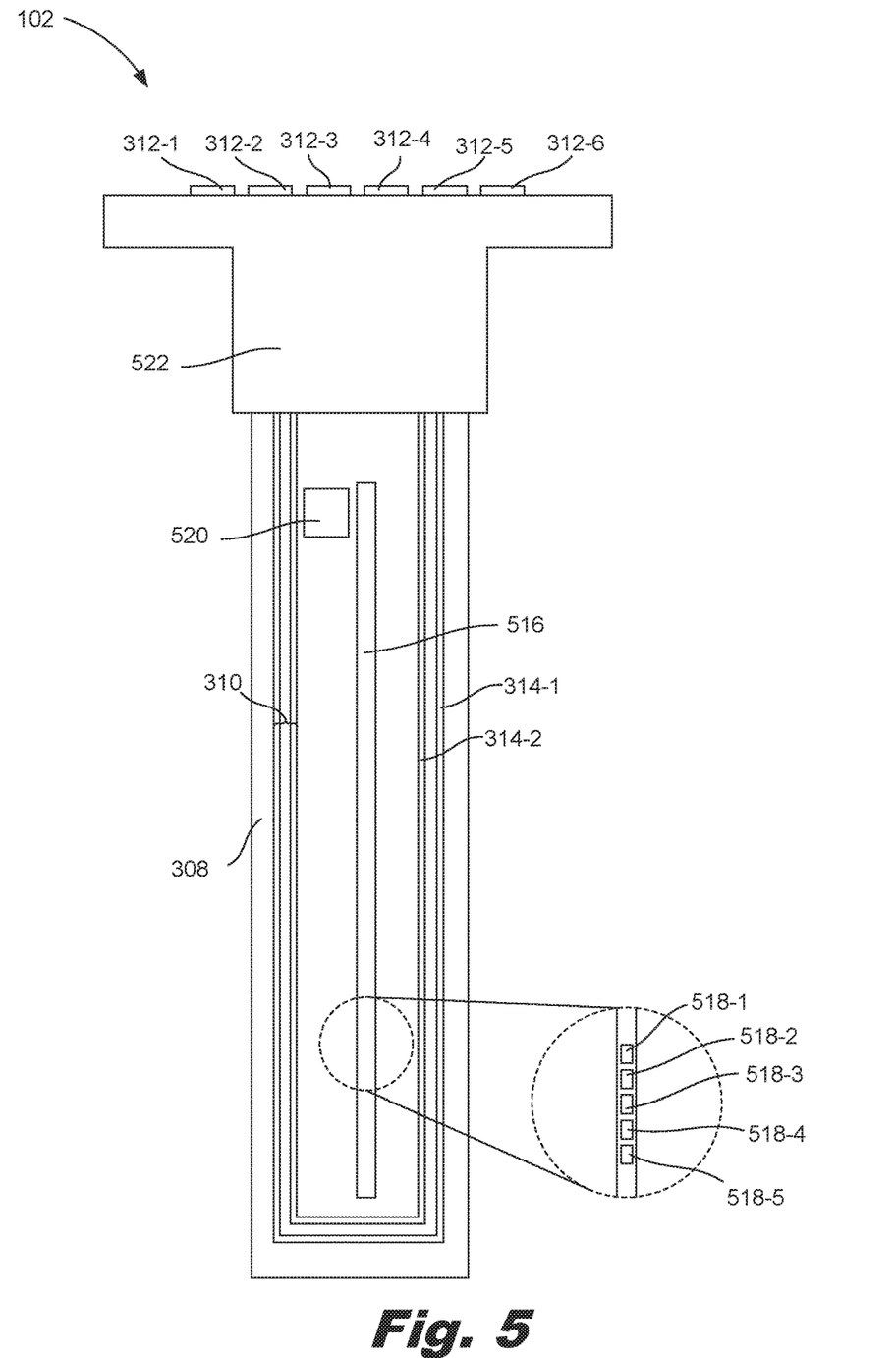
FIG. 5 is a top view of the fluid property sensing device, according to one example of the principles described herein.

FIG. 5 is a top view of the fluid property sensing device (102), according to one example of the principles described herein. In the example depicted in FIG. 5, the fluid property sensing device (102) includes a fluid level sensing die (516). In other words, similar to the fluid property sensing device (102), the fluid level sensing die (516) is also disposed on the substrate (308). Fluid level sensing components (518) disposed on the fluid level sensing die 9516) detect a level of fluid within the reservoir (FIG. 1,100).

More specifically, the fluid property sensing device (102) includes a substrate (308) having a trench (310) formed therein. The substrate (308) provides electrical connectivity between a fluid level sensing die (516), a capacitor, and electrical interconnects (312).

The fluid property sensing device (102) also includes a capacitor that is defined by electrodes (314-1, 314-2) placed on side walls of the trench (310). The capacitor detects a complex impedance that is indicative of the fluid properties. With such information, a determination of a fluid in the fluid reservoir (FIG. 1, 100) can be made, and subsequent processing, control, and analysis of the fluid and operation of the printing system can therefore be achieved.

In some examples, the fluid property sensing device (102) includes an integrated circuit (520) that includes additional processing functionalities. The integrated circuit (520) is electrically coupled to the sensing die (516) for example via wire bonding. The integrated circuit (520) may be an application specific integrated circuit that allows for the determination as to whether the fluid in the fluid reservoir (FIG. 1, 100) is counterfeit. The integrated circuit (520) may also be used to drive the sensing components (518), i.e., to drive the heaters and sensors described below. In this example, the information collected from the number of sensing components (518) is first passed to this integrated circuit (520) and then onto the electrical interconnects (312). The integrated circuit (520) is attached to the substrate (308) in any number of fashions. For example, an adhesive may be stamped onto the substrate (308) and the integrated circuit (520) disposed on the adhesive. While specific reference is made to a stamp adhesive, other methods may be used as well.

The fluid level sensing device (102) includes a sensing die (516). The sensing die (516) is a component of the fluid level sensing device (102) that has disposed thereon a number of sensing components (518). In some examples, the sensing die (516) is a sliver die that is thin, for example, less than 220 micrometers wide. The dimensions of the sensing die (516) may relate to one another using an aspect ratio, the aspect ratio being the ratio of the width of the sensing die (516) to the length of the sensing die (516). The sensing die (516) of the present application may have an aspect ratio of less than 1:50. In other words, the length of the sensing die (516) may be at least 50 times greater than a width of the sensing die (516). In another example the length of the sensing die (516) may be at least 100 times greater than a width of the sensing die (516). As a specific numeric example, the sensing die (516) may be less than 220 micrometers wide and longer than 22 millimeters.

The sensing die (516) is attached to the substrate (308) in any number of fashions. For example, an adhesive may be stamped onto the substrate (308) and the sensing die (516) is then placed on the adhesive. In this example, after the sensing die (516) and integrated circuit (520) are attached, the adhesive is cured so as to permanently affix the sensing die (516) and the integrated circuit (520) to the substrate (308). While specific reference is made to a stamp adhesive, other methods may be used as well.

Using such a thin sensing die (516) allows for improved silicon die separation ratios, eliminates silicon slotting costs, eliminates the fan-out chiclets, and avoids many process integration issues. Moreover, the sliver sensing die (516) offers precise control over the sensing die (516) geometry and supports fluid level sensing with multiple detection methods such as thermal fluid level sensing and impedance fluid level sensing.

As described above, the sensing die (516) includes a number of sensing components (518). For simplicity, in FIG. 5, a few sensing components (518-1, 518-2, 518-3, 518-4, 518-5) are depicted, but the sensing components (518) may extend along a length of the sensing die (516). Note that the sensing components (518) as depicted in at least FIG. 5 are not to scale and are enlarged to show their presence on the sensing die (516). Different types of sensing components (518) use different sensing methods to detect the level of fluid in the fluid reservoir (FIG. 1, 100). For example, impedance sensing components (518) detect the capacitance of a fluid with which the sensing component (518) is covered. As fluid conducts electricity at a different rate then air, the conductivity between sensing components (518) can be used to determine whether the conducting medium is air or liquid.

In another example, the sensing components (518) may use thermal operations to detect a fluid level. In this example, some of the sensing components (518) are heaters and some of the sensing components are heat sensors. The heaters are heating elements spaced along the sensing die (516). Each heater is close enough to a corresponding heat sensor such that heat emitted by an individual heater can be sensed by an associated heat sensor. Heat sensors are sensing elements that are also spaced along the length of the sensing die (516). Each of the heat sensors are sufficiently close to a corresponding heater such that the heat sensor detects or responds to the transfer of heat from a corresponding heater. The heat sensors output a signal which indicates the amount of heat transmitted to the particular heat sensor following and corresponding to a pulse of heat from an associated heater.

The amount of heat transmitted, and sensed by a heat sensor, will vary depending upon the medium through which the heat was transmitted prior to reaching the heat sensor. Using this system, and the known location of the heater and its heat sensor along the sensing die (516) the level of fluid within the fluid reservoir (FIG. 1, 100) can be determined. The sensing die (516) may be a high resolution sensing die (516) meaning it has a high density of sensing components (518). For example, the sensing die (516) may include over 80 sensors (518) per inch of length of the sensing die (516).

As can be seen in FIG. 5, in some examples, the trench (310) and corresponding electrodes (314), surround the fluid level sensing die (516). Doing so provides additional surface area of the capacitive plates so as to increase signal sensitivity when identifying a property of the fluid disposed therein.

The fluid property sensing device (102) also includes electrical interconnects (312) to output data collected from at least one of the integrated circuit (520), fluid level sensing die (516) and corresponding sensing components (518), and the electrodes (314). For example, the fluid level information gathered from the sensing components (518) can be passed to the user to indicate to the user when the fluid reservoir (FIG. 1, 100) is to be refilled or replaced. Still further, the data collected could be used by a printing system to prevent the printing system from depositing a printing fluid on a print medium when the sensing components (518) indicate that the fluid level in the fluid reservoir (FIG. 1,100) is below a threshold level. The fluid property information gathered from the electrodes (314) can be used to provide increased control over fluid usage, thus ensuring the use of certain types of fluids, certain qualities of fluids, or fluid from certain manufacturers.

With all these components attached, the sensing components (518), electrodes (314), integrated circuit, (520) and electrical interconnects (312) are coupled together such that signals can be interchanged between these components. For example, the sensing die (516) can be plasma treated and wire-bonded to the electrical interconnects (312). Similarly the integrated circuit can be plasma treated and wire-bonded to at least one of the sensing die (516) and the electrical interconnects (312).

In some examples, the fluid property sensing device (102) includes a sealing device (522). This sealing device (522) seals the fluid property sensing device (102) against a fluid reservoir (FIG. 1, 100) in which the fluid level sensing device (102) is inserted. In other words, the sealing device (522) provides a fluidic seal separating fluid contained within the fluid reservoir (FIG. 1, 100) from the electrical connection between the fluid property sensing device (102) and an external system. The sealing device (522) may be an overmolded plastic component. Accordingly, the sealing device (522) protects against mechanical damage to various components of the fluid property sensing device (102), specifically those disposed on the substrate (308) and also to fluidically seal the fluid in the fluid reservoir (FIG. 1, 100) so as to prevent leakage of fluid from the fluid reservoir. (FIG. 1, 100).

Figure 6:
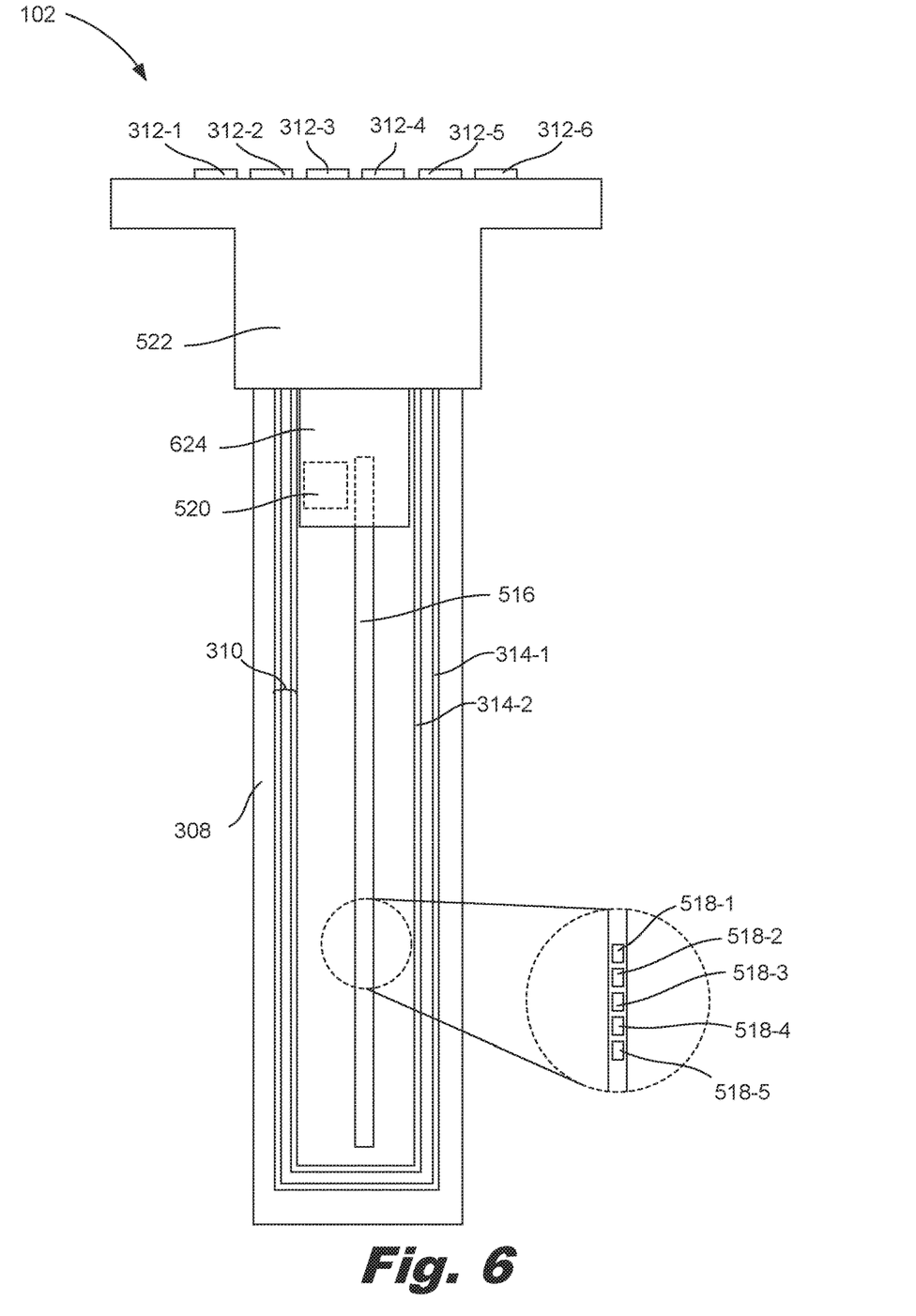
FIG. 6 is a top view of the fluid property sensing device, according to another example of the principles described herein.

FIG. 6 is a top view of the fluid property sensing device (102), according to another example of the principles described herein. In some examples, in addition to the components described above, the fluid property sensing device (102) further includes a protective cover (624) that is formed over at least an attachment point of the sensing die (516) and the substrate (308). The electrical connection between the sensing die (516) and the substrate (208) may be a number of small electrical wires. Such small wires are susceptible to mechanical damage during manufacture, shipping, assembly, and use. Accordingly, a cover (624) such as a wire bond adhesive or epoxy encapsulant can be disposed over this area to protect such components, while not interfering with electrical conduction along the lines disposed therein. Specifically, the sensing die (516) may be wire bonded to the substrate (308) the wire bond is then encapsulated with the cover (624), which cover (624) material may then be cured.

While FIG. 6, depicts the cover (624) extending 1) over a portion of the sensing die (216) and the substrate (210) and 2) over the integrated circuit (214), any number of cover (624) orientations may be used. For example, a single, or multiple covers (624) may encompass portions of the sensing die (516), the substrate (FIG. 3, 308), the integrated circuit (520), and the electrical interconnects (312). Specifically, the electrical connections between these components. The cover (624) provides protection against mechanical damage to the associated components.

Figure 7:
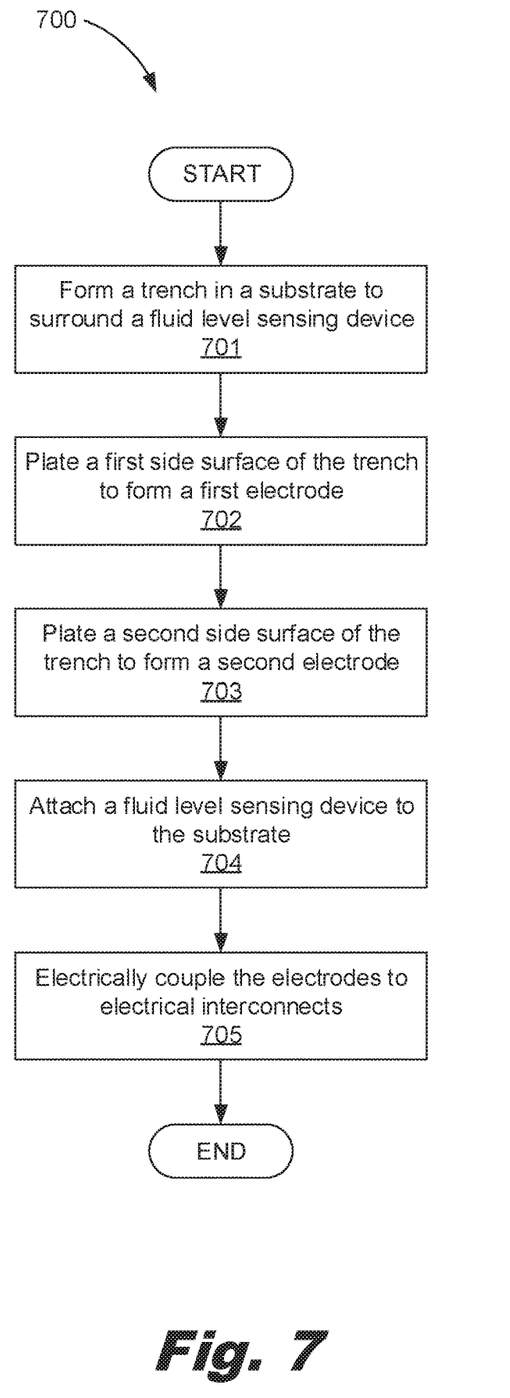
FIG. 7 is a flowchart illustrating a method of forming a fluid property sensing device, according to one example of the principles described herein.

FIG. 7 is a flowchart illustrating a method (700) of forming a fluid property sensing device (FIG. 1, 102), according to another example of the principles described herein. According to the method (700), a trench (FIG. 3, 310) is formed (block 701) in the substrate (FIG. 3, 308). Specifically, the trench (FIG. 3, 310) may be formed by the methods described above to surround a fluid level sensing die (FIG. 5, 516). Surrounding the fluid level sensing die (FIG. 5, 516) in this fashion provides additional surface area which increased surface area enhances the sensitivity of the electrodes (FIG. 3, 314) in taking complex impedance measurements.

Side surfaces of the trench (FIG. 3, 310) are then plated (blocks 701, 702) to form electrodes (FIG. 3, 314) that define the capacitor. This may be performed as described above in connection with FIG. 4.

A fluid level sensing die (FIG. 5, 516) can also be attached to the substrate (FIG. 3, 308). The fluid level sensing die (FIG. 5, 516) with its sensing components (FIG. 5, 518) can be attached using any number of methods including adhesive stamping. Attaching the fluid level sensing die (FIG. 5, 516) to the fluid property sensing device (FIG. 1, 102) thereby provides a single module, that 1) detects fluid levels in a fluid reservoir (FIGS. 1, 100) and 2) provides information regarding the properties of the fluid in the fluid reservoir (FIG. 1, 100). With these components attached, the electrodes (FIG. 3, 314), integrated circuit (FIG. 5, 520), and fluid level sensing die (FIG. 5, 516), are electrically coupled (block 705) to one another and to the electrical interconnects (FIG. 3, 312) to allow for data transfer between these various components.

Figure 8A:
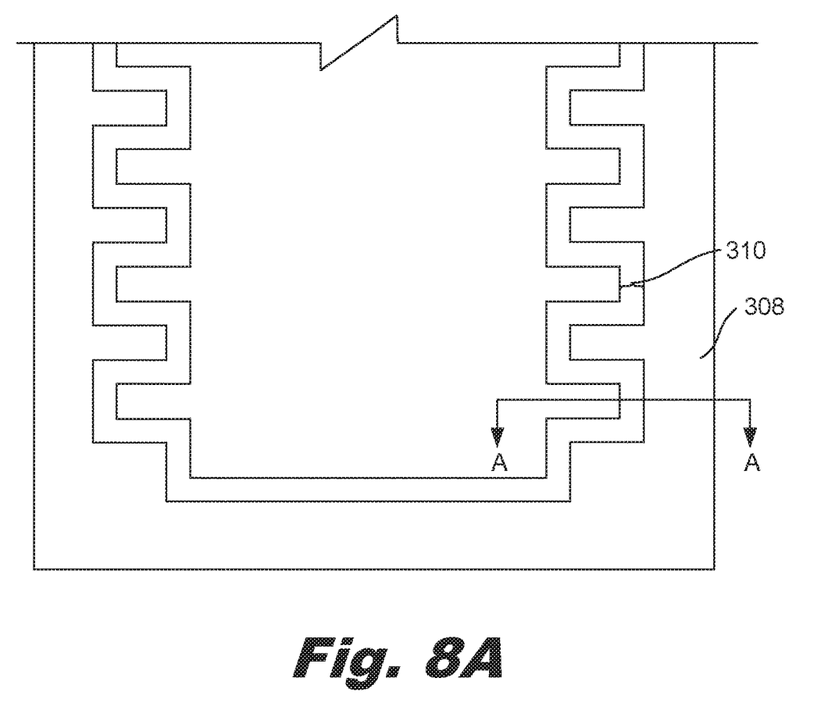
FIGS. 8A and 8B are views of a fluid property sensing device with a serpentine trench, according to one example of the principles described herein.
Figure 8B:
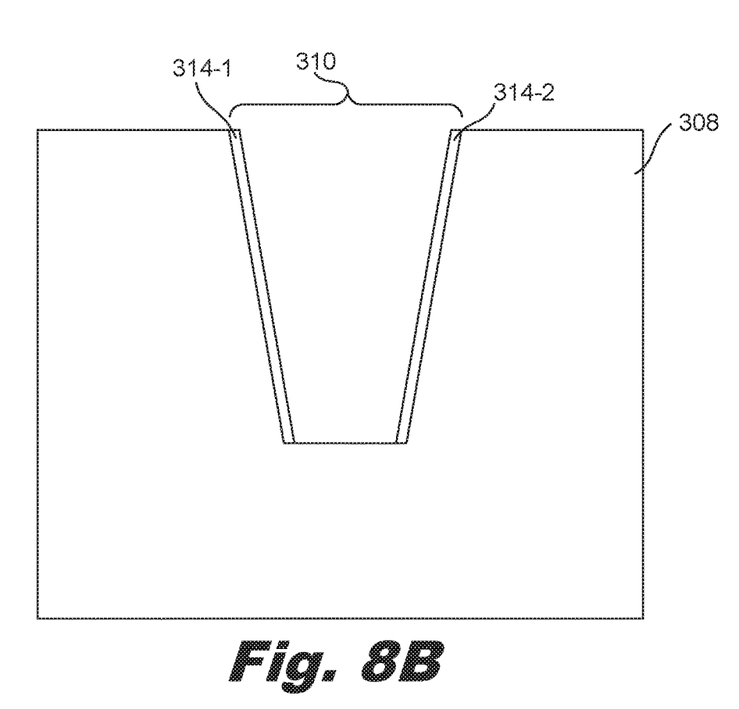

FIGS. 8A and 8B are views of a fluid property sensing device (FIG. 1, 102) with a serpentine trench (310), according to one example of the principles described herein. Specifically, FIG. 8A is a top view of a portion of the fluid property sensing device (FIG. 1, 102) and FIG. 8B is a cross-sectional view taken along the line "A-A" in FIG. 8A. As described above, the signal strength of the complex impedance can be increased by increasing the surface area of the electrodes (314-1, 314-2) that make up the capacitor. Accordingly, in one example, the trench (310) is a serpentine trench (310). Such a serpentine trench increases the surface area of the electrodes (314-1, 314-2) without increasing the overall size of the fluid property sensing device (FIG. 1, 102).

Increasing the surface area of the electrodes (314-1, 314-2) can also be achieved by increasing the depth of the trench (310). For example, FIG. 8B depicts the electrodes (314) and trench (310). However, to increase the sensitivity of the complex impedance measure, this trench (310) could be made deeper, thus allowing for a greater electrode (314) surface area, which increase in surface area would increase the signal strength of any measured complex impedance.

While FIGS. 8A and 8B depict specific ways to increase the surface area, i.e., serpentine trench (310) and increasing depth of the trench (310) other methods may also be used to increase the surface area of the electrodes (314).

Using such a device for sensing a fluid property 1) provides additional data, and therefore control over, fluids used in a fluid reservoir: 2) provides fluid property sensing via a device produced by a low cost, high volume, and simple manufacturing process; 3) provides a sensing device that supports fluid level sensing and fluid property sensing; 4) provides a large electrode to provide increased signal sensitivity; 5) provides a high resolution and high performance fluid level and property sensing platform; 6) supports multiple processes for detecting fluid levels; and 7) provides a fluid property sensing device that can be integrated as a module or on an interior surface of a reservoir; and 8) results in increased customer satisfaction due to the increased performance. However, it is contemplated that the devices disclosed herein may provide useful in addressing other matters and deficiencies in a number of technical areas. Therefore the systems and methods disclosed herein should not be construed as addressing any of the particular matters.

The preceding description has been presented to illustrate and describe examples of the principles described. This description is not intended to be exhaustive or to limit these principles to any precise form disclosed. Many modifications and variations are possible in light of the above teaching.

What is claimed is:

1. A fluid property sensing device comprising:
a substrate having a trench formed therein, the trench comprising a bottom surface and opposite side surfaces;
a first electrode disposed on a first side surface of the trench;
a second electrode disposed on a second side surface of the trench; and
an integrated circuit to receive output from the electrodes, wherein the first electrode and second electrode form a capacitor to measure a complex impedance of a fluid that fills a space between the first electrode and the second electrode, the integrated circuit to use the complex impedance to identify a property of the fluid.

2. The device of claim 1, wherein the fluid is ink.

3. The device of claim 1, wherein the substrate is an interior wall of a fluid reservoir.

4. The device of claim 1, wherein the substrate is part of a module to be inserted into a fluid reservoir.

5. The device of claim 1, further comprising a fluid level sensing die disposed on the substrate.

6. The device of claim 5, further comprising a cover over an attachment point between the fluid level sensing die and the substrate.

7. The device of claim 5, wherein the fluid level sensing die comprises heaters and heat sensors.

8. The device of claim 1, further comprising electrical interconnects to output data collected from the electrodes.

9. The device of claim 1, wherein the trench is a serpentine trench.

10. The device of claim 1, wherein the first and second side surfaces of the trench taper together toward the bottom surface of the trench.

11. The device of claim 1, further comprising a database that associates complex impedance values as measured by the capacitor with an identification of a corresponding fluid.

12. A method for forming a fluid property sensing device, comprising:
forming a trench in a substrate, wherein the substrate is an interior wall of a printer ink reservoir;
plating a first side surface of the trench to form a first electrode;
plating a second side surface of the trench to form a second electrode, the first electrode and the second electrode forming a capacitor defined by the side surfaces and a gap between the side surfaces; and
electrically coupling the electrodes to electrical interconnects.

13. The method of claim 12, wherein the second side surface and the first side surface are plated at the same time as:
the electrical interconnects; and
metal traces that electrically couple the electrodes to the electrical interconnects.

14. The method of claim 12, further comprising attaching a fluid level sensing die, having sensing components disposed thereon, to the substrate.

15. The method of claim 14, wherein forming the trench comprises forming the trench to surround the fluid level sensing die.

16. A fluid property sensing device comprising:
a substrate having a trench formed therein to provide:
electrical connectivity between a fluid level sensing die, a number of electrodes that define a capacitor, and electrical interconnects; and
mechanical protection of the fluid level sensing die;
the fluid level sensing die disposed on the substrate;
a number of sensing components disposed on the fluid level sensing die, the number of sensing components to detect a fluid level in a fluid reservoir;
a capacitor defined by electrodes placed on walls of the trench to detect a property of the fluid in the fluid reservoir;
an integrated circuit to output data collected form the number of sensing components to the electrical interconnects;
the electrical interconnects to output data collected from the integrated circuit and the capacitor; and
a sealing device to seal the fluid property sensing device against a fluid reservoir in which the fluid property sensing device is inserted.

17. The device of claim 16, wherein the trench surrounds the fluid level sensing die.

18. The device of claim 16, wherein the fluid level sensing die is less than 220 micrometers wide.

19. The device of claim 16, wherein the number of sensing components are thermal sensing components.

20. The device of claim 16, wherein the trench is a serpentine trench.

* * * * *